(12) United States Patent
Schilling

(10) Patent No.: US 10,456,288 B2
(45) Date of Patent: Oct. 29, 2019

(54) RAIL SYSTEM, FUNCTIONAL COMPONENT, AND ADAPTER ELEMENT

(71) Applicant: OTTO BOCK HEALTHCARE GMBH, Duderstadt (DE)

(72) Inventor: Matthias Schilling, Weissenborn-Luderode (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 553 days.

(21) Appl. No.: 14/773,738

(22) PCT Filed: Mar. 10, 2014

(86) PCT No.: PCT/EP2014/000604
§ 371 (c)(1),
(2) Date: Sep. 8, 2015

(87) PCT Pub. No.: WO2014/135281
PCT Pub. Date: Sep. 12, 2014

(65) Prior Publication Data
US 2016/0015551 A1    Jan. 21, 2016

(30) Foreign Application Priority Data

Mar. 8, 2013 (DE) .......................... 10 2013 003 936

(51) Int. Cl.
*A61F 5/01* (2006.01)
*A61F 5/058* (2006.01)
(Continued)

(52) U.S. Cl.
CPC ............ *A61F 5/05825* (2013.01); *A61F 5/01* (2013.01); *A61F 5/0104* (2013.01); *F16B 7/182* (2013.01);
(Continued)

(58) Field of Classification Search
CPC ...... A61F 5/05825; A61F 5/01; A61F 5/0104; A61F 2005/0158; A61F 5/0102; A61F 5/0118; A61F 5/0123; A61F 5/028; A61F 5/0106; A61F 5/0111; A61F 5/0127; A61F 13/06; A61F 13/061; A61F 5/03; A61F 5/058; A61F 5/05841; A61F 5/013; A61F 5/0193; A61F 5/02; A61F 2005/0165; A61F 2005/0174; A61F 2/605; A61F 2/64; A61F 2/6607; A61F 13/066; A61F 13/101; A61F 5/04; F16B 7/182; F16B 7/02
See application file for complete search history.

(56) References Cited

U.S. PATENT DOCUMENTS 1,265,635 A    5/1918   Eubank
2,463,124 A *  3/1949   Sims ..................... E04B 1/585
                                                          279/97

(Continued)

FOREIGN PATENT DOCUMENTS

BE           469500 A       12/1946
CN        201991888 U        9/2011
(Continued)

OTHER PUBLICATIONS

Beitz, W., "Dubbel, Taschenbuch fur den Maschinenbau," pp. G34-G37, Dec. 31, 2001.
(Continued)

*Primary Examiner* — Ophelia A Hawthorne
(74) *Attorney, Agent, or Firm* — Holland & Hart, LLP

(57) ABSTRACT

An orthopedic rail system which has a first component with a receiving element and a second component with a connection end for connecting to the receiving element. The receiving element has two opposing stop walls, and the connection end has two opposing lateral walls. The receiving element and the connection end can be connected to each other by at least one connection element such that the lateral walls rest against the stop walls in the connected state. The stop walls and the lateral walls each taper towards each other in a conical manner.

10 Claims, 19 Drawing Sheets

(51) Int. Cl.
*F16B 7/18* (2006.01)
*F16B 7/02* (2006.01)

(52) U.S. Cl.
CPC ......... *A61F 2005/0158* (2013.01); *F16B 7/02* (2013.01)

(56) References Cited

U.S. PATENT DOCUMENTS

| | | | |
|---|---|---|---|
| 2,567,577 A | | 9/1951 | Pariser |
| 3,913,570 A | * | 10/1975 | Madden .............. A61F 5/05825 602/5 |
| 8,839,676 B2 | | 9/2014 | Jarjour et al. |
| 2009/0163843 A1 | | 6/2009 | Win |

FOREIGN PATENT DOCUMENTS

| | | |
|---|---|---|
| CN | 102413795 A | 4/2012 |
| DE | 563009 | 10/1932 |
| DE | 20204917 U1 | 6/2002 |
| DE | 202007014602 U1 | 6/2008 |
| DE | 102007013438 A1 | 10/2008 |
| GB | 2383555 A | 7/2003 |
| RU | 2391945 C1 | 6/2010 |
| SU | 94203 A1 | 11/1951 |

OTHER PUBLICATIONS

English translation of PCT International Search Report for PCT International Patent Application No. PCT/EP2014/000604, dated Aug. 25, 2014.

* cited by examiner

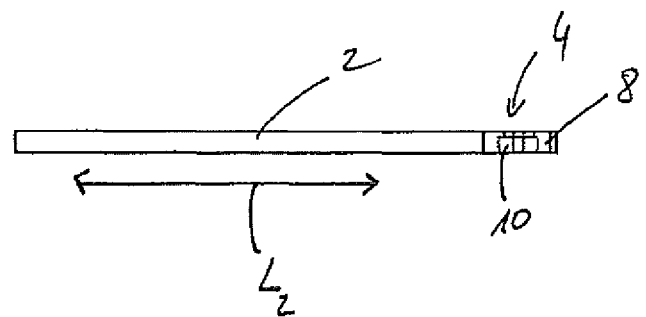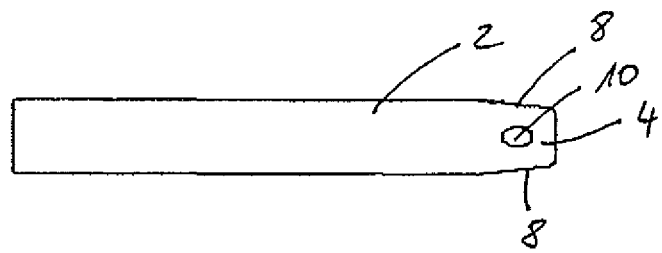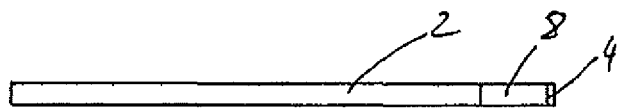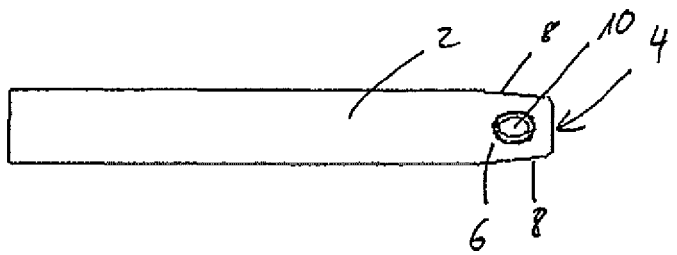
Fig. 4

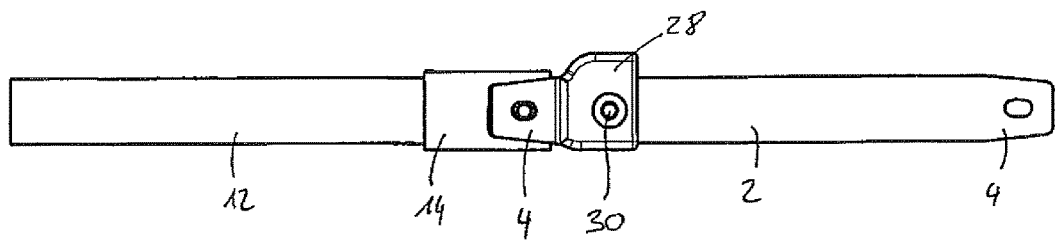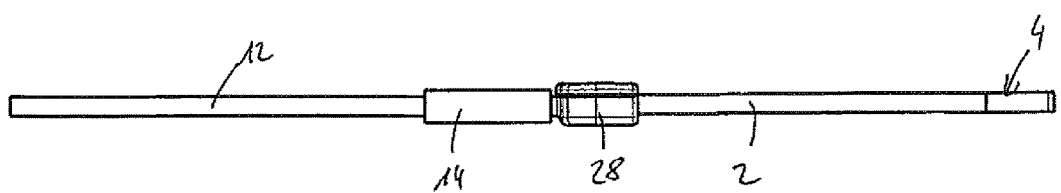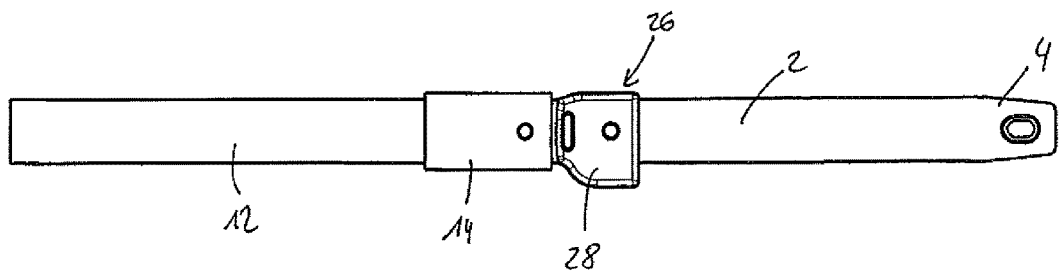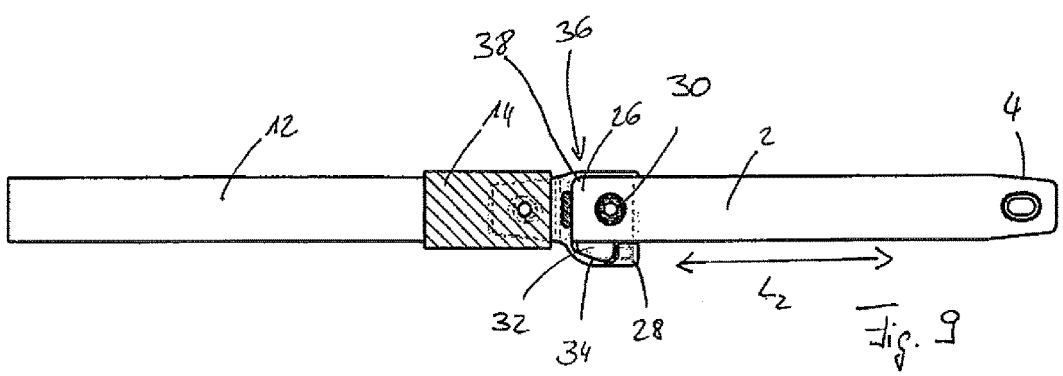
Fig. 9

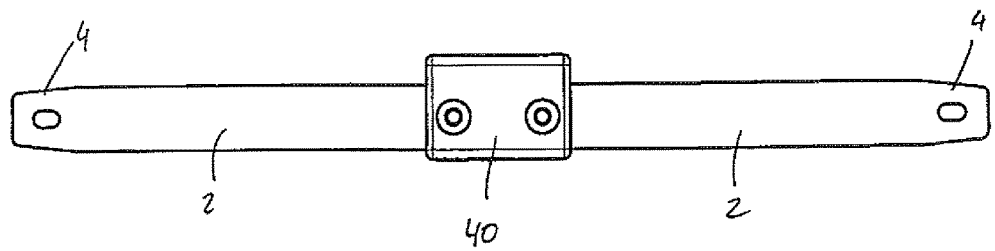
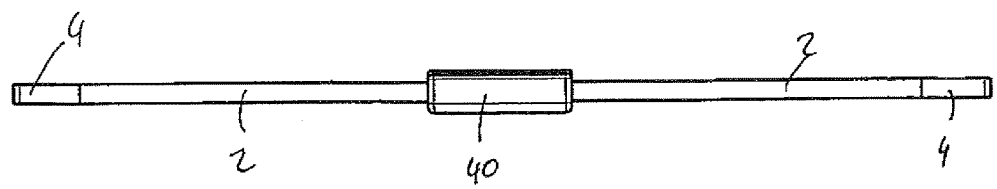
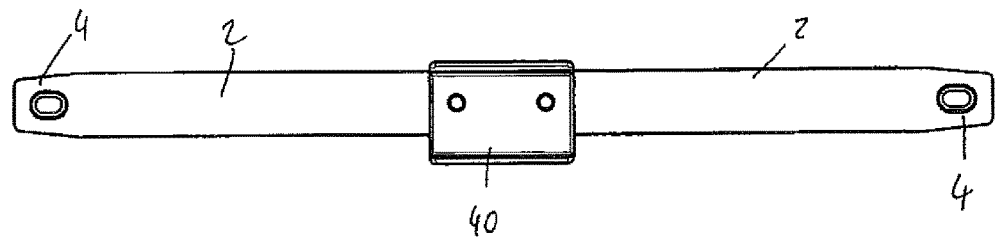
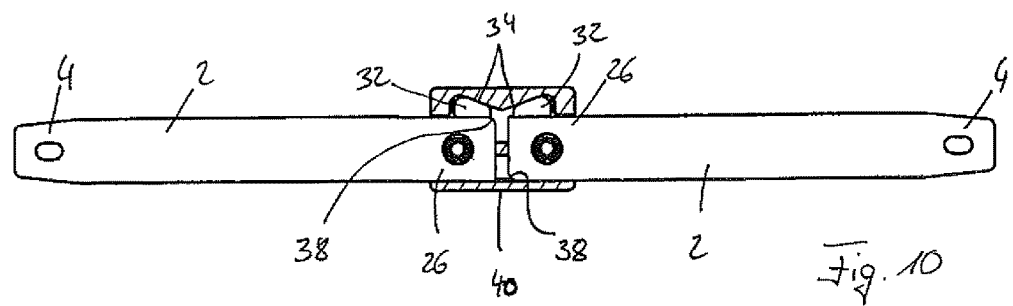
Fig. 10

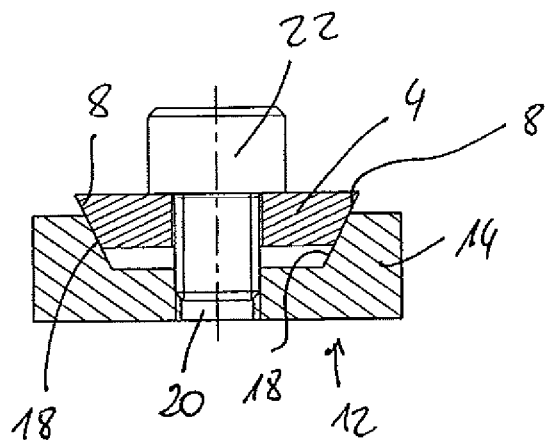
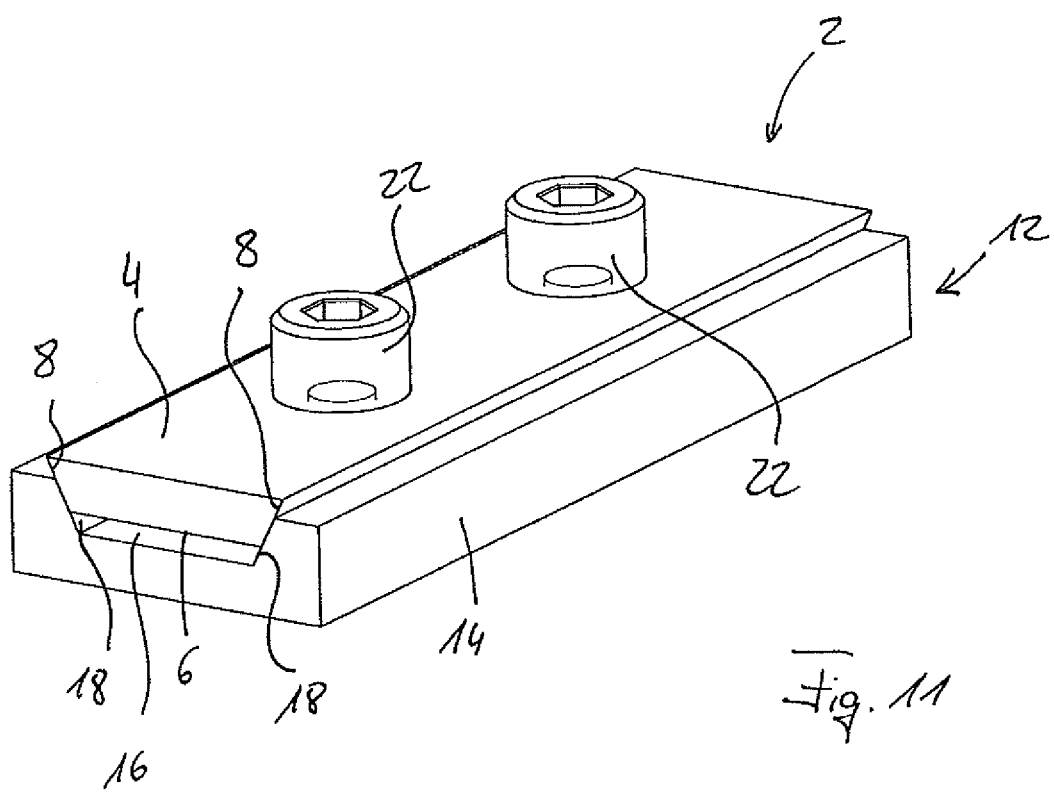
Fig. 11

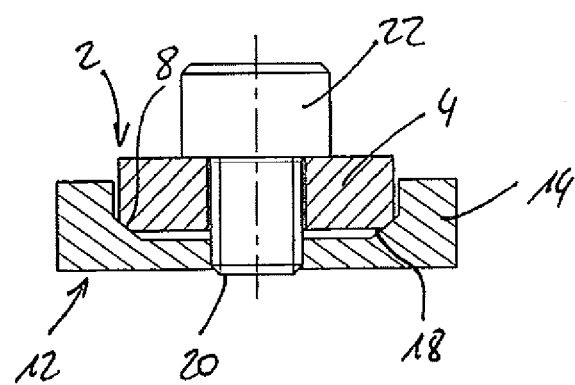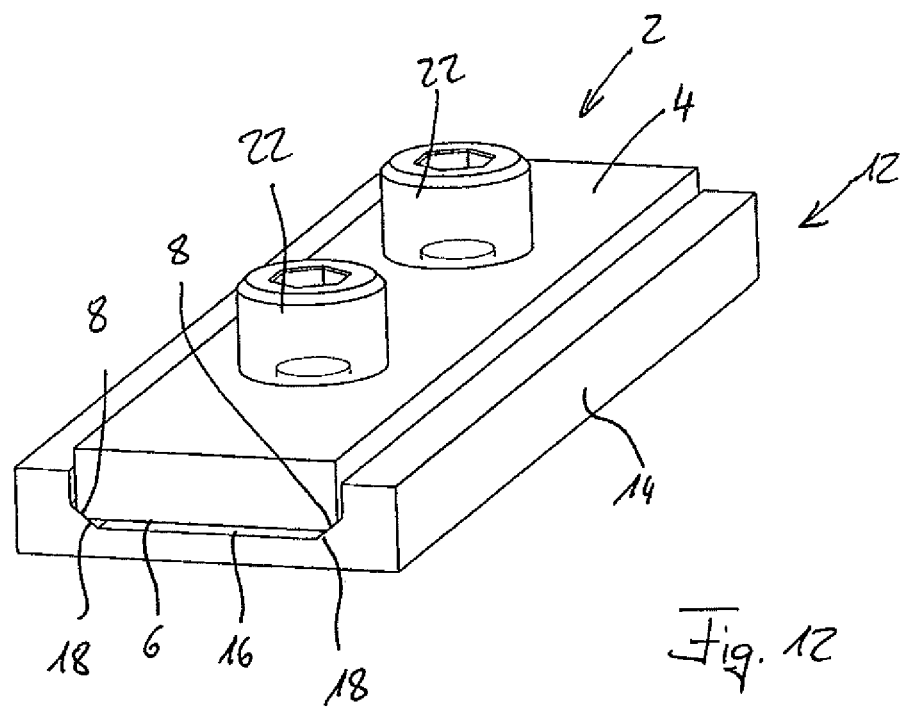
Fig. 12

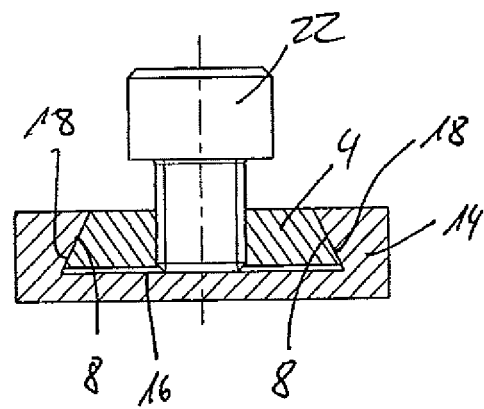
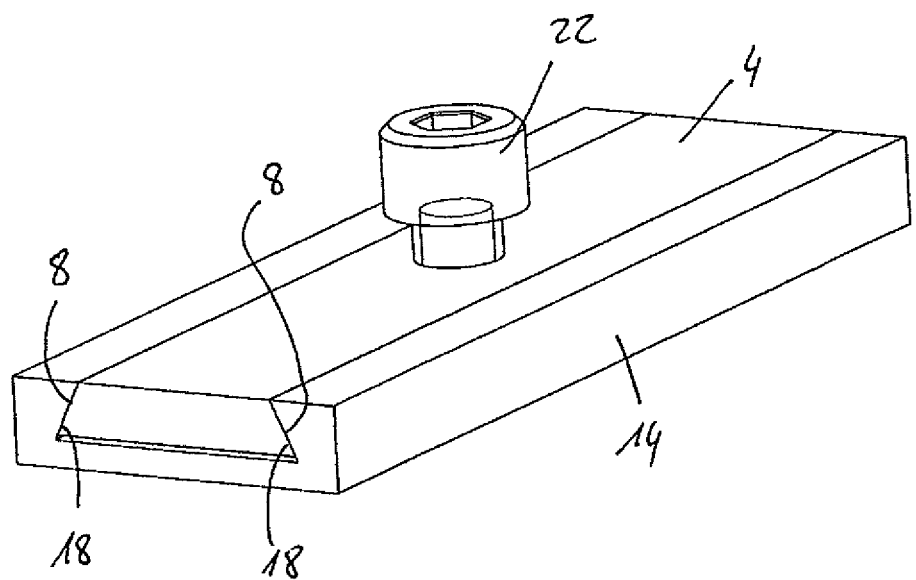
Fig. 13

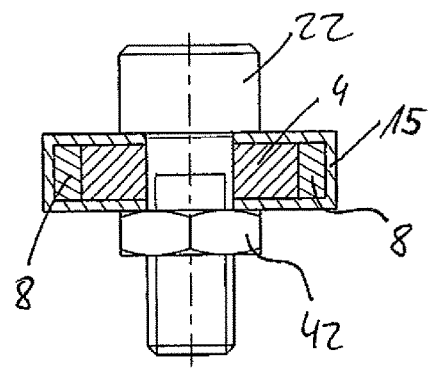
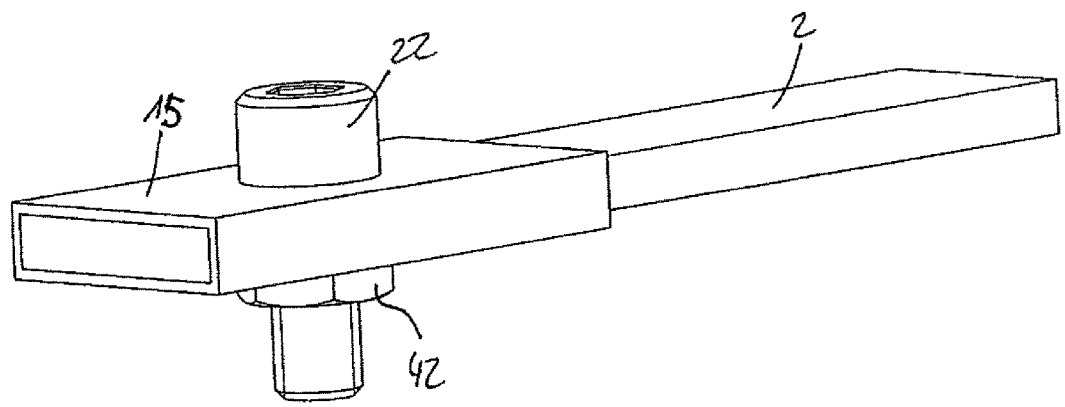
Fig. 14

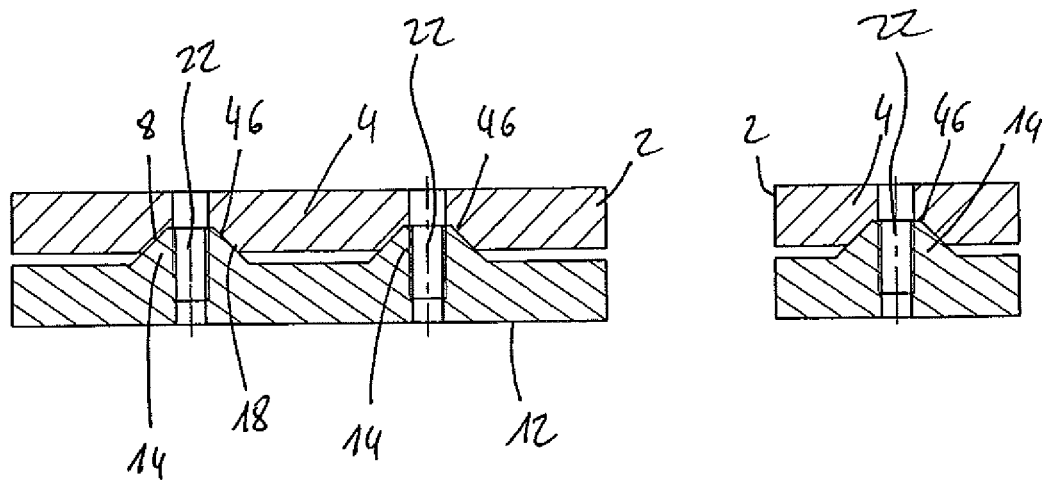
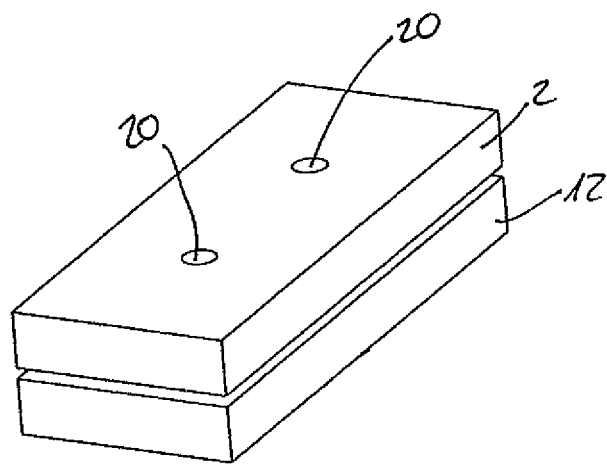
Fig. 16

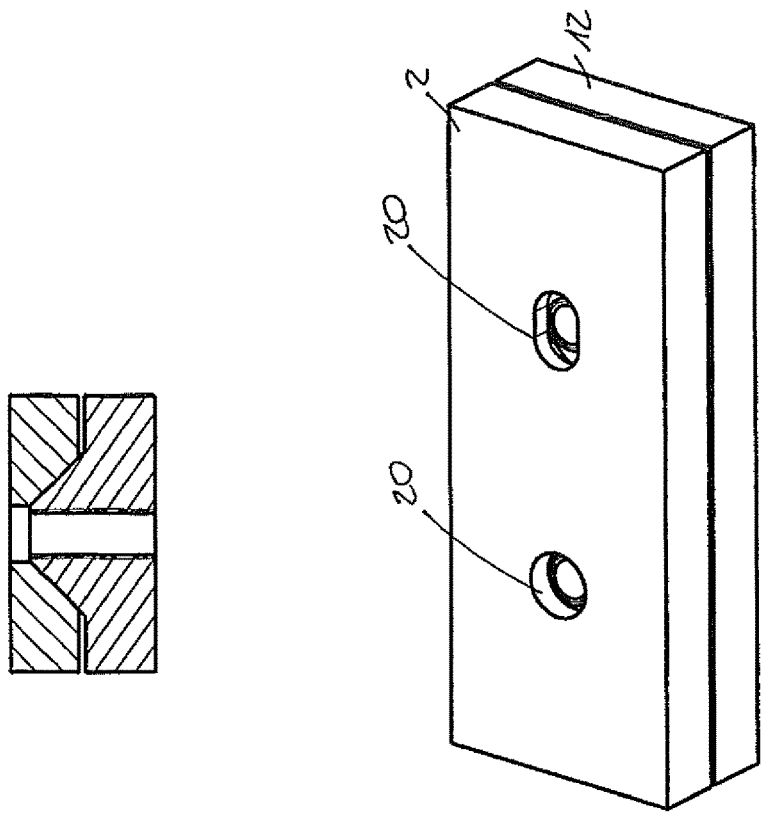
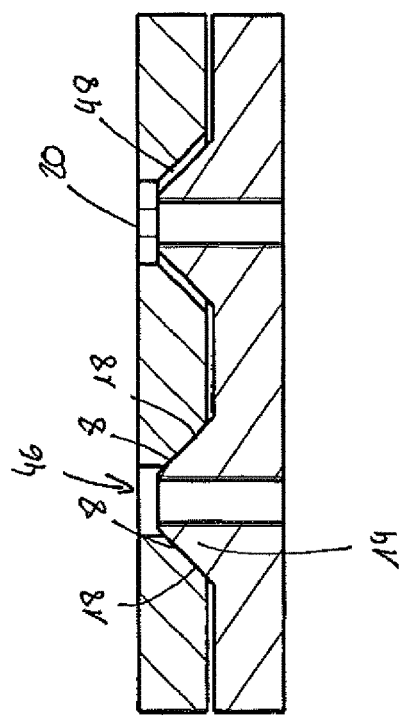
Fig. 43

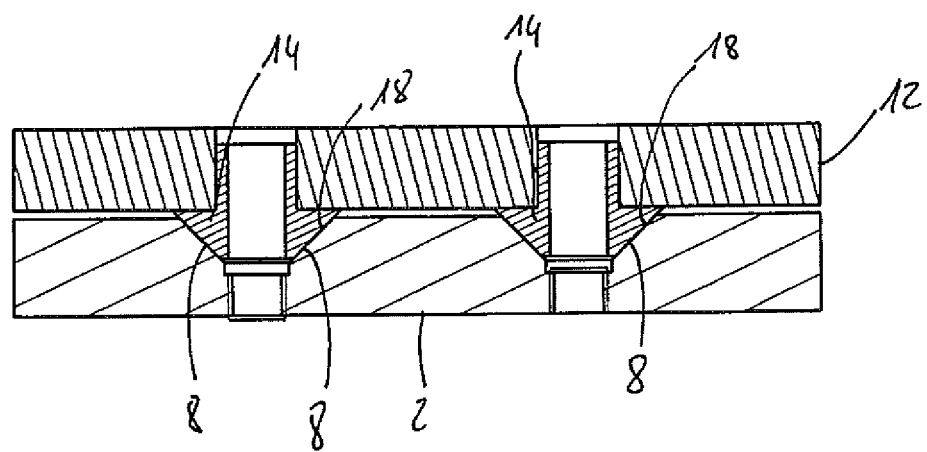
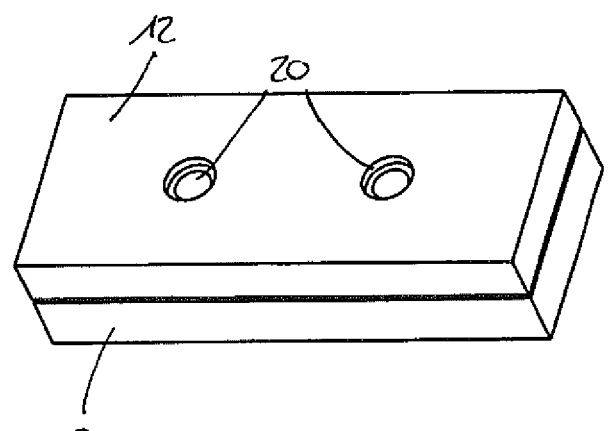
Fig. 18

RAIL SYSTEM, FUNCTIONAL COMPONENT, AND ADAPTER ELEMENT

TECHNICAL FIELD

The invention relates to an orthopedic rail system, in particular for an orthosis or a prosthesis, which rail system has a first component with a receiving element and a second component with a connection end for connecting to the receiving element, wherein the receiving element has two stop walls lying opposite each other, the connection element has two lateral walls lying opposite each other, and the receiving element and the connection end are connectable to each other by at least one connection element, such that the lateral walls bear on the stop walls in the connected state. The invention also relates to a functional component for an orthopedic rail system, and to an adapter element for connecting the two components of the rail system.

BACKGROUND

Many orthoses comprise several components that are arranged at different places on the body of the person wearing the orthosis. Thus, for example, a knee orthosis is arranged on the thigh and on the lower leg of the wearer. These individual different components are connected to each other by a rail system of the type in question here, wherein this rail system can, for example, comprise freely pivotable or lockable joints, which are connected to corresponding rails, but can also comprise stiff connections between two rails. In order to obtain an individual adaptation of the orthosis to the physique of the wearer, the individual rails that interconnect the various components of the rail system and of the orthosis have to be individually prepared for the wearer or cut into lengths. Two components of a rail system are conventionally connected by connecting the connection end of one component, for example of a rail, to a receiving element of another component which, for example, can likewise be a rail or one of the aforementioned joints.

The receiving element has two parallel lateral walls which lie opposite each other and between which the connection end of the respective other component is positioned. To obtain a connection that is as firm and secure as possible and to achieve a comfortable and secure feel for the person wearing the orthosis, it is necessary for the individual components to be connected to each other in a manner free of play. This is important not only in the final orthosis but of course also during the work carried out in testing a new orthosis. For example, the lateral walls and the underside of the connection end of the second component are usually laboriously reworked, for example by secondary filing or secondary grinding, in order to achieve the best possible match of the connection end to the receiving element. In addition, the two components are screwed together via at least two screws, these being intended to achieve a particularly secure connection, since the screws take up at least some of the acting forces. A disadvantage is that the production of such matching components is complex, time-consuming and therefore expensive, and moreover, when the orthosis is being tested out, the corresponding connection ends have to be reworked again each time the dimensions of individual components are changed. Testing out the orthosis is in this case likewise lengthy and uncomfortable for the wearer unless a connection that is free of play is provided during the testing.

Alternatively or in addition to this, it is known to provide compensating plates or intermediate components that are placed or fitted between the two components that are to be connected, for example in the receiving element of the first component, in order to compensate for manufacturing tolerances and to ensure that the two components are connected in a manner free of play. This has the disadvantage that a large number of different compensating plates have to be kept in stock in order to be able to compensate for different manufacturing tolerances. These components can get mislaid, such that it is not possible to ensure a permanent connection free of play, particularly after the individual components have optionally frequently been released from each other.

For the final orthosis, it is known, in addition to or as an alternative to a special reworking of the connection end of the various components, to additionally adhesively bond the components that are adapted to one another and optionally screwed onto one another. For this purpose, a special glue is often used which, in a further protracted and therefore time-consuming and costly method step, has to be allowed to set. A disadvantage of this is that the connection cannot be undone again without being destroyed, such that the orthosis, once joined together, can only be modified with great difficulty and adapted to possibly altered conditions of the patient.

To ensure that the two components can be easily released from each other, it is known from the prior art for example, to design a rail with an insert element, which is introduced into a recess provided for this purpose. A locking element is in this case pressed out from its rest position counter to a spring force of a spring element, and it snaps back into its rest position as soon as the insert element has reached its final position. The connection is locked by the spring element that has snapped back. However, it is also a disadvantage here that a very exact match of the individual components to one another has to be ensured if the connection locked by the snapped-back spring element is to be free of play. Therefore, the problem addressed by the invention is that of further developing a rail system as per the preamble of claim 1 in such a way that a connection that is free of play can be achieved easily and quickly, while easy releasability of the connection is nevertheless also ensured.

SUMMARY

The problem addressed is solved by the invention in that the orthopedic rail system as per the preamble of claim 1 is characterized in that the stop walls and the lateral walls, respectively, taper conically toward each other. This means that the distance between the two lateral walls and between the two stop walls in each case continuously decreases in one direction or remains constant in parts. This can take place, for example, in a direction parallel to a longitudinal direction of the component or for example in a direction perpendicular thereto.

It is thus ensured that, independently of any existing inaccuracies and manufacturing tolerances, a connection that is free of play can be achieved even without additional adhesive bonding, and also, for example, with just a single connection element. By virtue of the fact that the stop walls and also the lateral walls respectively taper conically toward each other and that the distance between both stop walls and the distance between the two lateral walls consequently decreases, the two components to be connected to each other can be arranged relative to each other in such a way that a stop wall and a lateral wall bear on each other across the entire surface area. At the moment when the respective other stop wall comes into contact with the respective other lateral wall, a rotation about an axis perpendicular to the base or to the underside of the two components to be connected to each other is no longer possible. In this case, a single connection element is sufficient to ensure a connection that is free of play.

The contact across the entire surface area can be achieved in particular if the one stop wall and the one lateral wall that are intended to bear on each other across the entire surface area extend rectilinearly or have the same radius of curvature. However, a connection that is free of play can still be achieved even if the respective walls have different radii of curvature.

In a preferred embodiment of the rail system, the receiving element and the connection end are able to be positioned steplessly relative to each other. Through the combination of the conically tapering lateral walls and stop walls and the possibility of positioning the receiving element and the connection end steplessly relative to each other and also of connecting them in each position thus reached, the problem addressed by the invention is solved in a particularly simple way. By virtue of the fact that the receiving element and the connection end are able to be positioned steplessly relative to each other and are able to be connected to each other, both components are also able to be connected to each other particularly in the position in which they bear on each other in a manner free of play. Thus, in a particularly simple way in design terms, inaccuracies arising as a result of manufacturing tolerances can be compensated and, despite these inaccuracies, the two components can be connected to each other in a manner free of play.

Preferably, the receiving element has a base and the connection end has an underside, wherein the underside bears on the base in the connected state of the two components. By virtue of the fact that base and underside likewise bear on each other in the connected state, insertion of replacement plates or similar replacement parts is not necessary. By undoing the connection element, which can be a screw for example, the receiving element can be easily and quickly released from the connection end and, therefore, the first component can be easily and quickly released from the second component. This allows the two components to be safely anchored on each other without play even during the testing and the adaptation of the orthosis to the body of the patient.

In a particularly advantageous embodiment of the present invention, the receiving element is a rail box.

In a particularly advantageous embodiment of the rail system, it has at least one connection element for connecting the receiving element to the connection end. It is also possible to use exactly one connection element. A particularly simple embodiment is obtained in this way.

Advantageously, the first component has a first longitudinal direction, wherein at least one stop wall encloses, with the first longitudinal direction, an angle different than 0°. The first longitudinal direction is in particular the direction in which the connection end of the second component is inserted into the receiving element of the first component. If, for example, the first component is a rail, this longitudinal direction advantageously corresponds to the direction in which the rail has its longest extent. The advantage of the present invention is already afforded in this case if just one of the stop walls encloses, with the first longitudinal direction, an angle different than 0°. The remaining second stop wall can then be configured in the usual way, for example parallel to the longitudinal direction.

In an advantageous embodiment of the rail system, the second component has a second longitudinal direction, wherein at least one lateral wall encloses, with the second longitudinal direction, an angle different than 0°. The second longitudinal direction often corresponds in this case to the direction in which the connection end of the second component is pushed into the receiving element of the first component. In this case too, it is sufficient if just one lateral wall encloses, with the second longitudinal direction, an angle different than 0°.

However, it has proven advantageous if both stop walls and/or both lateral walls enclose, with the respective first longitudinal direction or second longitudinal direction, an angle different than 0°. It has proven particularly advantageous here if the angles between the stop walls and the first longitudinal direction and between the lateral walls and the second longitudinal direction are identical.

The identical nature of the angles for the two stop walls and for the two lateral walls has the effect that both the first component and also the second component can be used in two different orientations. Thus, for example, the connection end can be inserted into the receiving element in two orientations pivoted through 180° to each other. Assembly is thus made easier, since both components can no longer be "wrongly" joined together. Moreover, for the production of the respective component, the same tool can be used for both walls. In this way, it is possible to produce the receiving element in one setup, as a result of which, on the one hand, the cost of production is reduced and, on the other hand, the precision with which the two lateral walls can be produced relative to each other is increased.

If the angles between the two stop walls, on the one hand, and the two lateral walls, on the other hand, are also identical, this leads to a particularly good accuracy of fit and a particularly good reproducibility of the connection. It is thus ensured that the two longitudinal directions of the first component and second component, for example after connection of the two components by insertion of the connection end into the receiving element, extend parallel to each other or at a predefined desired angle to each other.

In a preferred embodiment of the rail system, the receiving element and the connection end are able to be positioned steplessly relative to each other in two mutually perpendicular directions and are connectable to each other. This ensures that a wide variety of deviations and fault tolerances can be compensated. Preferably, these two directions extend parallel to the underside of the connection end and parallel to the base of the receiving element.

In the production of the connection end of the second component, the lateral walls of the connection element have to be produced, for example, by means of a milling machine. One possible deviation on account of inaccuracies in the production lies in what is called the angle deviation. This means that the finished lateral wall encloses, for example with the longitudinal direction of the component, an angle that is different than the desired angle. Another possible deviation lies in the position of the lateral wall which, for example, can be displaced by the milling machine removing too much or too little material. In this case, the lateral wall has, for example, the desired angle in relation to the longitudinal direction of the respective component, but it is located at a position displaced relative to the central axis of the component. An actual deviation from the desired form of the connection end will generally consist of a combination of both deviations.

However, it should be noted here that position deviations caused by removal of too much or too little material usually occur much more often, and with greater deviation, than is the case of angle deviations. Independently of the deviation that occurs, it is always possible, in particular with the displaceability ensured in two different directions, to achieve a connection that is free of play unless the deviations go beyond a predefined tolerance range.

Advantageously, the receiving element is connected releasably to the first component. In this case, for example, different receiving elements can be kept in stock, which can be connected for different purposes to the first component. For example, it is thus conceivable to connect different receiving elements to the first component, which ensure that the second component to be connected to the first component extends at a defined angle in relation to the first component. Thus, for example, the angle between the first longitudinal direction and the second longitudinal direction of the respective components can be adjusted and adapted to the needs of the respective patient.

It is of course also advantageous to provide a releasable connection end component which is connectable to one end of a conventional component that does not have a connection end. Both the connection end component and also a separate receiving element can then be connected to a component, for example according to the prior art, for example before the orthosis is tested out and adapted. The connection end component has a connection end in the already described form and, consequently, can be inserted with this connection end into a receiving element of the already described form and locked there. Thus, rail systems according to the prior art can also be retrofitted, such that the advantage according to the invention can also be exploited for these systems.

A functional component according to the invention for an orthopedic rail system is characterized in that the functional component has a receiving space for receiving an end of the component, which receiving space has at least one displacement surface and a displacement wedge mounted displaceably on the latter.

It has proven particularly advantageous in this case that the end of the component can be firmly clamped, by displacing the at least one displacement wedge along the at least one displacement surface, when it is received in the receiving space. For this purpose, it is expedient to design the at least one displacement wedge such that it can be locked in different positions. Advantageously, these different positions are steplessly adjustable. If one end of a component is now received in the receiving space, the at least one displacement wedge can be displaced along the at least one displacement surface and thereby ensures that the end of the component is firmly clamped in the receiving space. The at least one displacement wedge has in this case been displaced to such an extent that a connection that is free of play is obtained between the two components. In this state, the at least one displacement wedge can be locked such that both the displacement wedge and also the end of the component are held securely in this position. Of course, further securing means, for example screws or similar devices, can be present in order to stabilize the thereby established position of the end of the component in the receiving space of the functional component.

The functional component can in this case, for example, be part of a joint, a rail of an orthopedic rail system, or any other component.

In a preferred embodiment, the at least one displacement wedge for firmly clamping the end of the component is displaceable in a direction perpendicular to a longitudinal direction of the component. In this way, for example, the receiving space can be designed to be open in one direction, for example to the top, while the at least one displacement wedge is arranged on a cover element, by which this opening of the receiving space can be closed. For example, the at least one displacement wedge is inserted in this case into a space between a lateral wall of the receiving space and the end of the component located in the receiving space, such that, with deeper insertion of the wedge into this space, the end of the component is displaced until it is clamped between the at least one displacement wedge and a further component. This further component can also be a further displacement wedge, such that the end of the component can be clamped between two displacement wedges. As an alternative to this, the displacement wedge can also be present as a separate component, which is pressed by the cover element into the desired position.

The displacement surface preferably encloses, with a longitudinal direction of the component, an angle different than 0°. If such a receiving element or a connection end component is now to be secured on one of the components, an end of the component is inserted into the receiving space. The end of the component and the displacement wedge are in this case advantageously matched to each other in such a way that they have contact surfaces with which they bear on each other, these contact surfaces being designed parallel to each other.

In this design too, by displacement of the displacement wedge along the displacement surface, the component can be clamped in the receiving space and adapted and then additionally fixed, for example by means of a screw connection. The receiving element or the connection end component is then firmly connected to the first component. This connection can also be advantageously designed to be easily releasable. However, the connection between the respective component and a receiving element or the connection end component can take place even before the orthosis is tested out and adapted to the patient, and therefore easy releasability is not of overriding importance in this case. It has proven advantageous if the functional component is a receiving element or a connection end component for an orthopedic rail system described here.

An adapter element according to the invention for connecting the first component to the second component of a rail system, with which the first component can be connected with one end, lying opposite the receiving element, to an end of the second component lying opposite the connection end, is characterized in that the adapter element has two receiving spaces for receiving the end of the first component and the end of the second component, which each have at least one displacement surface and a displacement wedge mounted displaceably on the latter. The displacement surfaces preferably enclose, with the respective longitudinal direction of the first component and second component, an angle different than 0°. As in the case of the already described receiving element and the connection end component, both components can here be connected to the adapter element. This is effected by a displacement of the respective displacement wedge, such that the respective component is clamped in the adapter element and is then secured, for example, by connection elements that are present, such as screws. An adapter element of this kind is advantageous particularly for cases in which rails or components are to be interconnected that do not have a connection end with conically tapering lateral walls. Therefore, rail systems according to the prior art can also be equipped with the adapter element according to the invention and can thus be connected to each other. Of course, an adapter element of this kind can ensure not only a rigid connection between two components but also equip a wide variety of types and forms of joints, for example locking joints, or joints with angle limits in different directions.

With the separate adapter element, it is also possible in particular to be able to carry out length adjustment in a particularly simple way. Of the component in question, in this case the end at which there are no conically tapering lateral walls can be shortened in particular. This end is shortened in a way known from the prior art, such that the components can be adapted to the desired length. The end, in particular after being shortened, does not have to be provided with conically tapering lateral walls in this case, and therefore the desired shortening can be carried out particularly easily and quickly by the orthopedic technician on site. This does not adversely affect the quality of the connection that is obtained free of play between the individual components.

In all of the embodiments described, it is advantageous if the lateral walls and the underside enclose a right angle. It is also advantageous if the stop walls and the base also enclose a right angle. However, other configurations are of course also conceivable.

BRIEF DESCRIPTION OF THE DRAWINGS

Illustrative embodiments of the present invention are explained in more detail below with reference to a drawing in which:

FIG. 4 shows the component from FIG. 1 in different views,

FIG. 9 shows connected components of a rail system in different views, FIG. 10 shows two components connected via an adapter element, in different views, FIGS. 11 to 14 show connections of two components of a rail system in a schematic 3D view and a sectional view for different illustrative embodiments of the present invention, FIGS. 16 to 19 show further views of interconnected components in a schematic 3D view and a sectional view.

DETAILED DESCRIPTION

Figure 1:
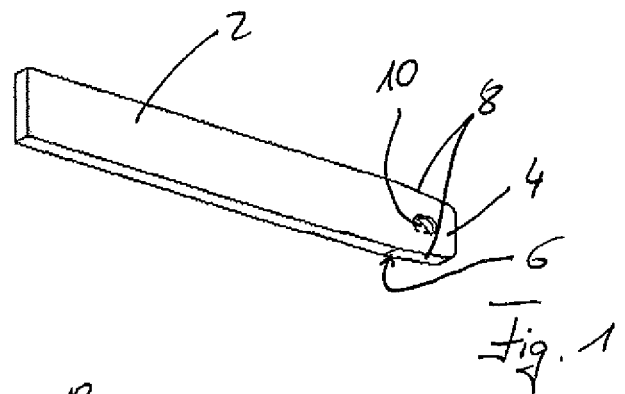
FIG. 1 shows a component with a connection end.

FIG. 1 shows a second component 2, at one end of which a connection end 4 is located. The connection end 4 has an underside 6 and two lateral walls 8. It will be seen that the two lateral walls 8 taper conically toward each other such that, in the illustrative embodiment shown, the distance between the two lateral walls 8 decreases. In the connection end 4 there is a bore 10, which is configured as an oblong hole. A connection element can be guided through the latter in order to connect two components to each other.

Figure 2:
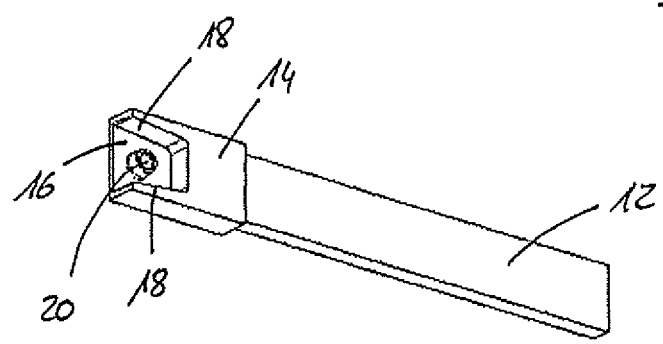
FIG. 2 shows a component with a rail box.

FIG. 2 shows a first component 12, at one end of which a receiving element 14 in the form of a rail box is located. The latter has a base 16 and two stop walls 18, which lie opposite each other and taper conically toward each other. Consequently, the distance between the two stop walls 18 also decreases. A receiving device 20 is located centrally, which receiving device 20 can be designed, for example, as a threaded bore.

Figure 3:
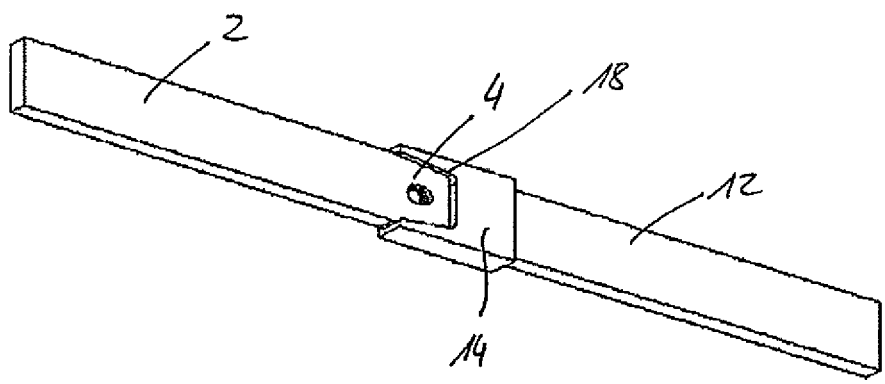
FIG. 3 shows the two components from FIGS. 1 and 2 in the connected state.

FIG. 3 shows the first component 12 and the second component 2 in the state when joined to each other. It will be seen that the connection end 4 is received in the rail box. The underside 6 bears on the base 16 in this case. Moreover, the lateral walls 8 of the connection end 4 are in contact with the stop walls 18 of the rail box. The bore 10 lies flush above the receiving device 20, such that a connection element (not shown in FIG. 3) inserted here secures the first component 12 and the second component 2 to each other. It will be seen that the bore 10 is configured as an oblong hole, such that the two components 2, 12 are displaceable relative to each other.

Since the lateral walls 8 and also the stop walls 18 are designed tapering conically toward each other, it is ensured, independently of any existing inaccuracies within the context of manufacturing tolerances, that the two components 2, 12 are always connected to each other in a manner free of play.

FIG. 4 shows the second component 2 from FIG. 1 in different views. The view at the very top is a sectional view along a second longitudinal direction $L_2$. The right-hand part of this view shows the connection end 4 with an angled lateral wall 8. The bore 10 extends through this connection end 4.

Below this there is a plan view of the second component 2 with the connection end 4 and the bore 10 located therein. The lateral walls 8 tapering conically toward each other are also shown here. Below this is a side view of the second component 2.

The view at the very bottom of FIG. 4 shows the second component 2 in a view from underneath. It is thus possible to see here the underside 6 of the connection end 4, and the two lateral walls 8. The bore 10 is made in two different depths, as can already be seen from the sectional view shown in the upper part of FIG. 4. A connection element to be arranged therein can in this way be recessed for example with a screw head in the second component 2.

Figure 5:
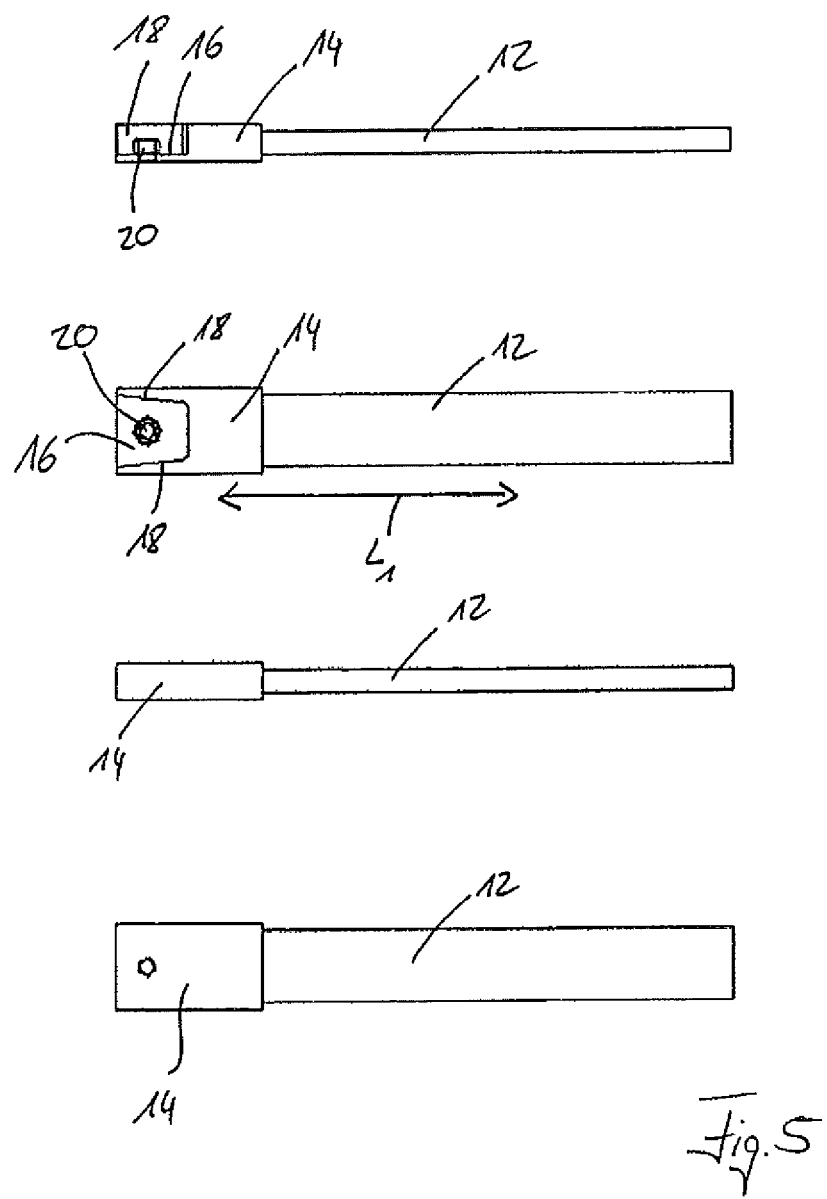
FIG. 5 shows the component from FIG. 2 in different views.

FIG. 5 shows the first component 12 in the same views as the second component 2 in FIG. 4. At the very top, therefore, is the sectional view through the first component 12 and the rail box 14. A plan view is shown below this. It can be seen particularly clearly from this plan view that the two stop walls 18 are designed tapering conically toward each other and, in this case, both enclose an angle different than 0° to a first longitudinal direction $L_1$. Below this, in the side view of the first component 12 with the rail box 14, it can be seen particularly clearly that the installation space required for the rail box 14 can be extremely small. Since the illustrative embodiment shown is provided with just one receiving device 20 for precisely one connection element, the rail box 14 can be designed much smaller than rail boxes known from the prior art.

Figure 6:
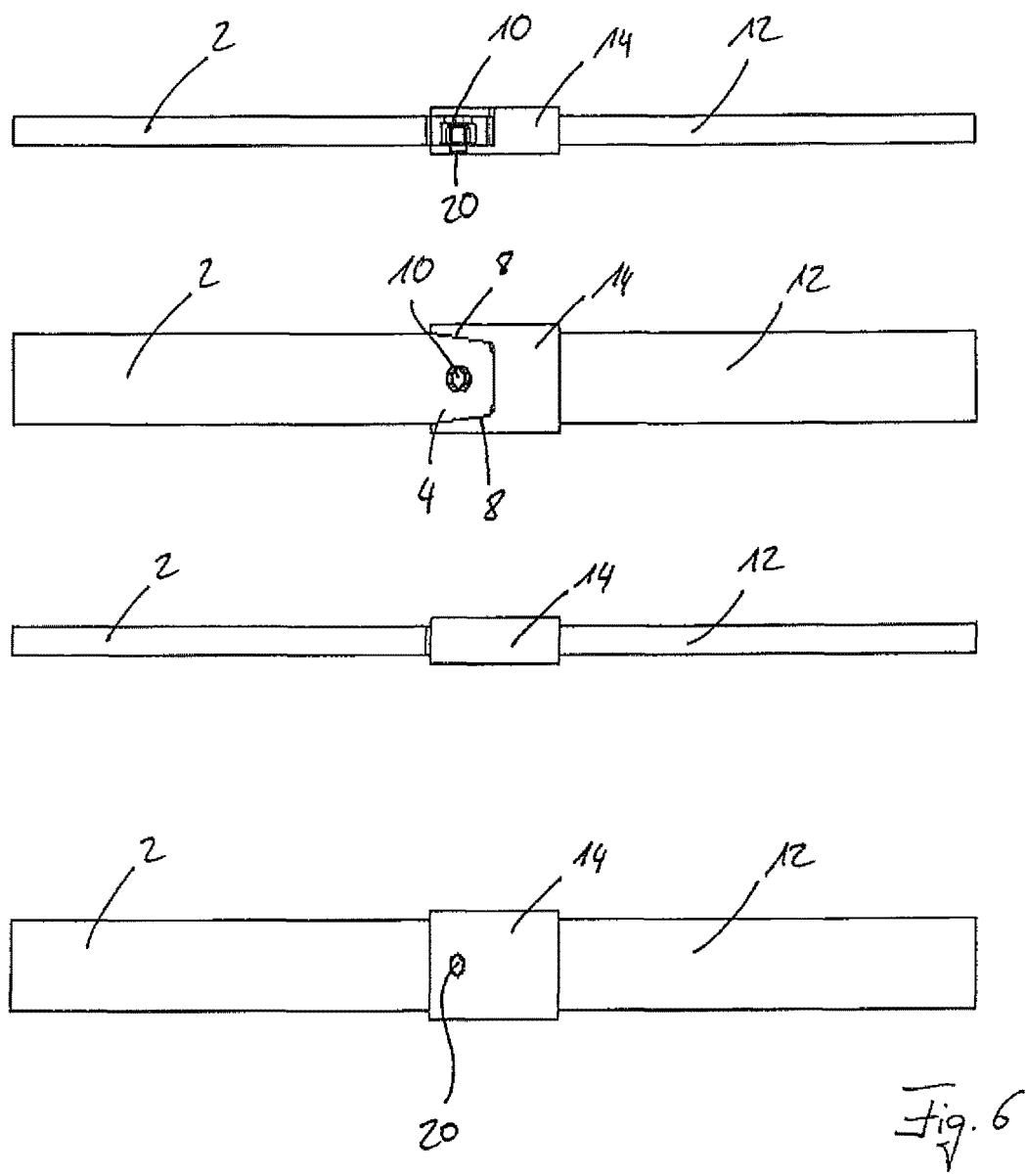
FIG. 6 shows the connected components from FIG. 3 in different views.

FIG. 6 shows the two components 2, 12 in the connected state, in the views already known from FIGS. 4 and 5. The connection end 4 of the second component 2 is inserted into the rail box 14 of the first component 12. The lateral walls 8 bear on the stop walls 18, and the underside 6 bears on the base 16. With this design, the two components 2, 12 are connected to each other in a way that is structurally compact but free of play and secure.

Particularly in the plan view shown second from the top and depicting the two components 12, 2 joined together, it will be seen that the bore 10 is not only configured as an oblong hole in the direction of the respective longitudinal direction $L_2$, $L_1$ but is also larger, in a direction transverse thereto, than would be necessary for a connection element. This means that displaceability is also possible in a direction perpendicular to the respective longitudinal direction $L_1$, $L_2$, and the two components can be secured to each other in each position thus adopted. This has the effect that it is possible to compensate in particular for variations in the amount of material removed.

Figure 7:
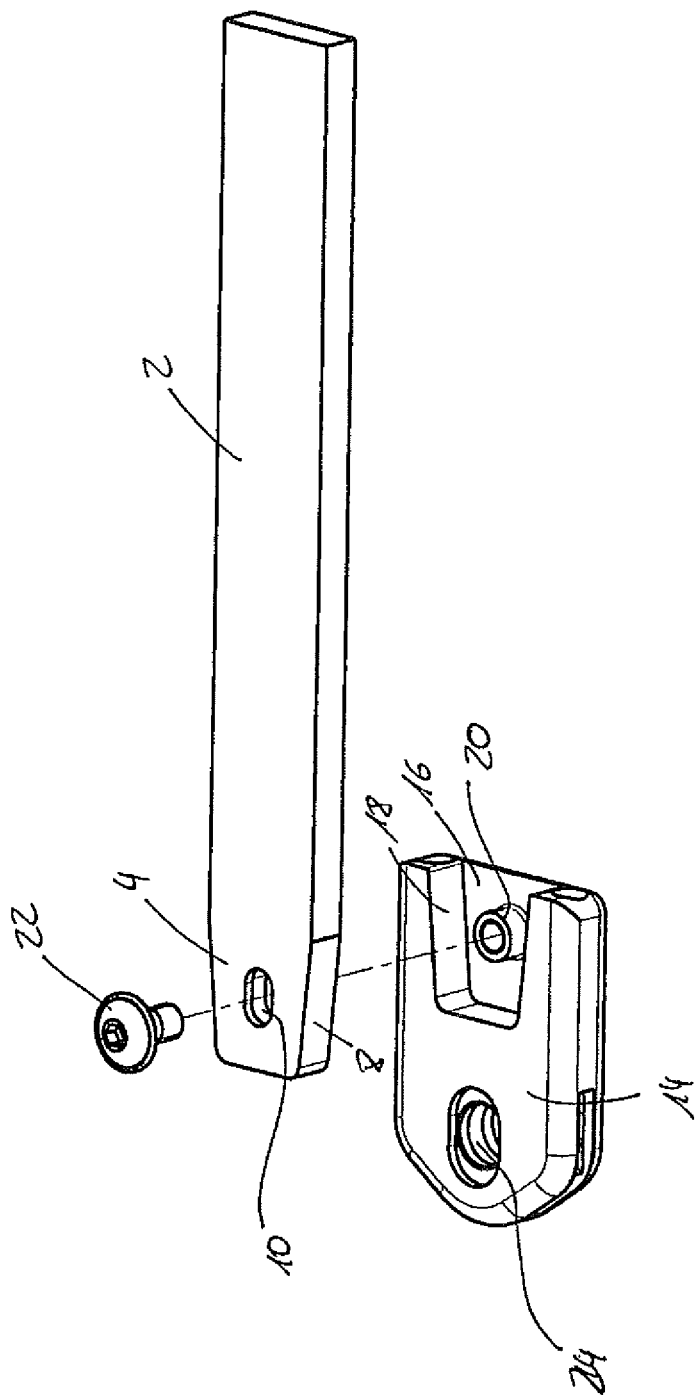
FIG. 7 shows a component with a connection end and a rail box.

FIG. 7 shows the second component 2 with the connection end 4 and with a separate rail box 14 to be secured thereon. A connection element 22 can be seen which is guided through the bore 10 of the connection end 4 and is screwed into the internal thread of the receiving device 20. This permits a particularly simple and secure connection of the two components to each other.

The rail box 14 has a recess 24 through which a further connection element (not shown) can be guided in order to secure the rail box 14 on the first component 12.

Figure 8:
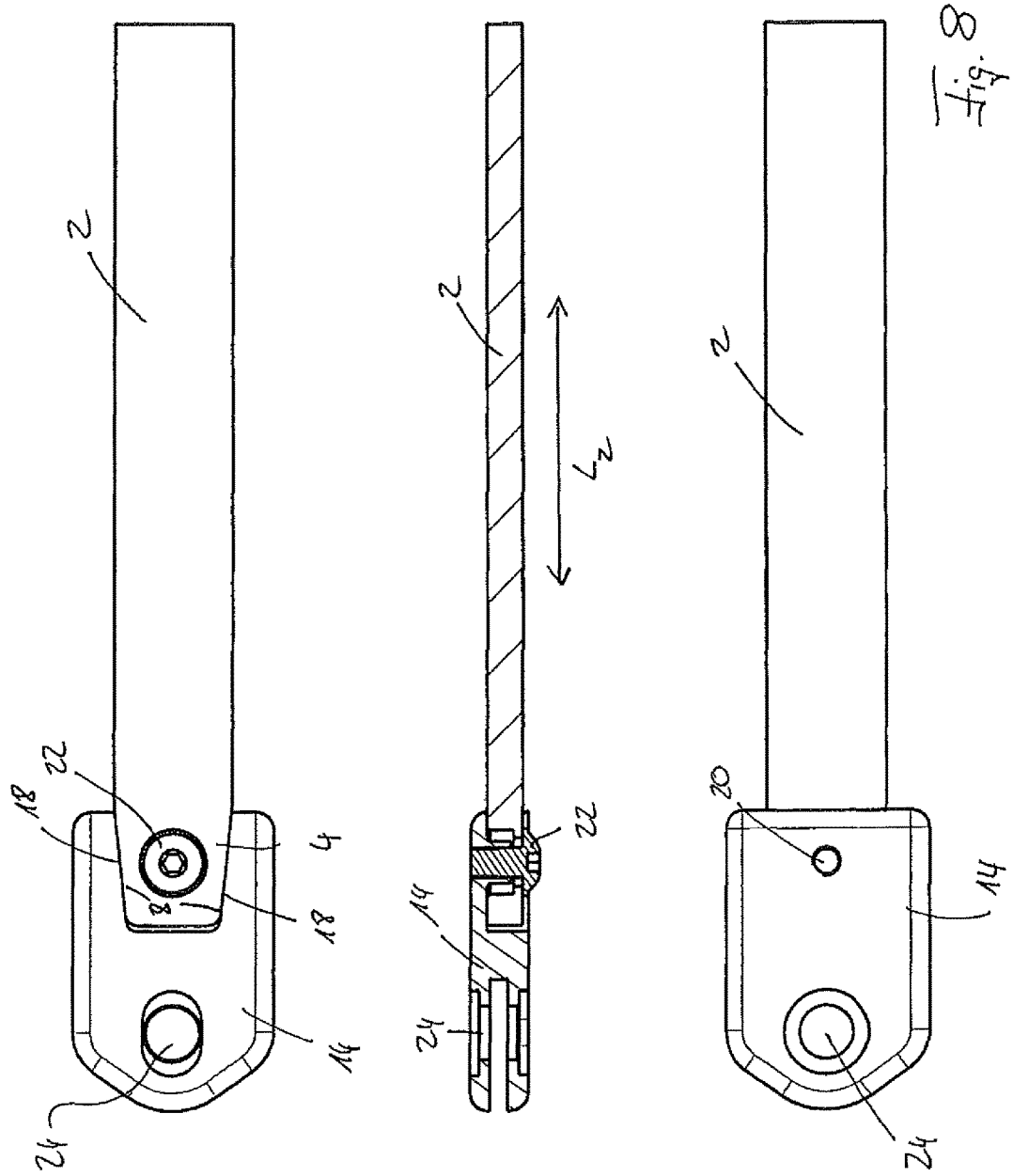
FIG. 8 shows the two components from FIG. 7 in the connected state in different views.

FIG. 8 shows the elements from FIG. 7 in the connected state and in different views. A sectional view along the longitudinal direction $L_2$ is shown in the middle. At the top is a plan view, and at the bottom a view from underneath. The connection element 22 is guided through the bore 10 and the receiving device 20 and thus connects the second component 2 to the rail box 14.

Alternatively, for example, the pivot axis for a joint can also extend through the recess 24, which joint can in this particularly simple way be arranged on the second component 2.

FIG. 9 shows four different views of the first component 12 on which the rail box 14 is located. A plan view, a side view, a view from underneath and a longitudinal sectional view are shown from the top downward. The second component 2 with the connection end 4 is located on the right in each view. However, in the illustrative embodiment shown, the second component 2 is arranged on the rail box 14 not with the connection end 4 but instead with the opposite end 26. At this end, a separate connection end component 28 is arranged which is secured on the end 26 of the second component 2 via a second connection element 30. In the view at the very top of FIG. 9, it will be seen that the connection end component 28 likewise has a connection end 4, which is designed like the connection end 4 of the second component 2. This connection end 4 is arranged in the rail box 14 of the first component 12 in the manner already described.

In the view at the very bottom of FIG. 9, it will be seen that the connection end component 28 has a displacement wedge 32, which is arranged in a recess provided for it and is displaceable in the direction of the second longitudinal direction $L_2$. The displacement wedge 32 for this purpose bears on a displacement surface 34 of the connection end component 28.

By a displacement of the displacement wedge 32 along the displacement surface 34, which has an angle to the second longitudinal direction $L_2$ different than 0°, the clear width of the receiving space 36 into which the end 26 of the second component 2 is received decreases. In this way, the second component 2 can be clamped inside the receiving space 36 and can be fixed by the additional second connection element 30.

In the illustrative embodiment shown, the end 26 has a rounded corner 38. Since the opposite corner is not rounded and the receiving space 36 of the connection end component 28 is adapted to this configuration, the end 26 can be inserted into the receiving space 36 only in one orientation. As regards the functionality, it is immaterial at which corner the rounded corner 38 is arranged and what actual shape this corner has, as long as the configuration permits a clear differentiation of the two corners and the receiving space 36 is adapted to this configuration.

Of course, instead of the connection end 4 on the connection end component 28, a rail box 14 can also be provided. The component then is not a connection end component 28 but a separate rail box 14 which can be arranged at one end of a component that is not designed as a connection end 4. Through these separate components, conventional rails and components according to the prior art can also be furnished with the advantages of the present invention.

FIG. 10 shows two second components 2 with connection ends 4 which are connected to each other via an adapter element 40. FIG. 10 also shows the views already known from FIG. 9. The two second components 2 are introduced via their ends 26 into the adapter element 40. This can clearly be seen especially in the lowermost sectional view in FIG. 10. The adapter element 40 has two displacement wedges 32, which are each arranged displaceably on a displacement surface 34. In this way, the operating principle already known from FIG. 9 can be achieved and the ends 26 of the second components 2 can be clamped in the adapter element 40. The two ends 26 each have a rounded corner 38, which ensures that they can be introduced into the adapter element 40 only in one orientation.

FIG. 11 shows, in the lower part, the schematic three-dimensional arrangement of the first component 12 with the rail box 14, with a second component 2 arranged thereon and having a connection end 4. The connection end 4 has two conically tapering lateral walls 8 which, in the state shown in FIG. 11, bear on the two stop walls 18 of the rail box 14. It will be seen that, in the illustrative embodiment shown, the underside 6 does not bear on the base 16. The two components 2, 12 are connected to each other via two connection elements 22, which are designed here as screws. The same arrangement is shown in a sectional view in the upper part of FIG. 11. In this view, it is again clear that the conically tapering lateral walls 8 bear on the likewise conically tapering stop walls 18 and that the connection element 22 is fitted in the receiving device 20 which, in the illustrative embodiment shown, is provided with an internal thread.

FIG. 12 shows a similar view. Here too, the lower part of FIG. 12 shows the first component 12 with the rail box 14, and the second component 2 with the connection end 4. In contrast to the embodiment shown in FIG. 11, the conically tapering lateral walls 8 and the likewise conically tapering stop walls 18 do not occupy the entire area of the respective surface of their component 2, 12. However, they taper conically in part and, in the illustrative embodiment shown, bear on each other. It is also clear here that the underside 6 does not have to bear on the base 16. The upper part of FIG. 12 shows a sectional view through the connection shown in the lower part. By means of the connection element 22 which engages in the receiving device 20, the two components 2, 12 are clamped against each other, resulting in a stable connection free of play.

FIG. 13 shows a further illustrative embodiment of the rail box 14 and of the connection end 4. This connection end 4 also has two conically tapering lateral walls 8, which bear on two likewise conically tapering stop walls 18. However, the direction in which the two walls conically taper is rotated through 180° in relation to the illustrative embodiments shown in FIGS. 11 and 12. In the illustrative embodiment shown in FIG. 13, only a single connection element 22 is provided by which the two components are clamped onto each other. The upper part of FIG. 13 shows the situation in the form of a sectional view. In this illustrative embodiment, the connection element 22 is guided through the recess in the connection end 4 of the second component 2, but it does not engage in a recess in the first component 12 or in the rail box 14 thereof. Instead, the connection element 22 bears, with the end shown toward the bottom in FIG. 13, on the base 16 of the rail box 14, such that further screwing in of the connection element 22 downward in the illustrative embodiment shown in FIG. 13 results in a force that acts on the second component 2 or the connection end 4 thereof and is directed upward. In this way, the two components 2, 12 are clamped together in this example too.

The lower part of FIG. 14 shows an additional element 15 which is designated as a lock and into which a connection end 4 of the second component 2 is inserted. The additional element 15 can be connected rigidly to the second component 2 or can be designed as a separate component. Instead of the circumferentially closed design shown in FIG. 14, the additional element 15 can also consist, for example, of two plate elements to be arranged one at the top and one at the bottom. The additional element 15 is closed all around its circumference, such that it completely surrounds the connection end 4 (not shown) of the second component 2. Here too, the connection between the two components 2, is locked via a connection element 22, which is again designed as a screw. In the illustrative embodiment shown in FIG. 14, a nut 42 is arranged on the connection element 22 and is used to apply the required force.

The upper part of FIG. 14 again shows a sectional view from which it can clearly be seen that the additional element 15 is closed circumferentially. The connection element 22, with the nut 42 arranged thereon, extends both through the additional element 15 and also through the connection end 4 of the second component 2. Different hatching indicates the two conically tapering lateral walls 8, which extend analogously to the component 2 shown for example in FIG. 1.

Figure 15:
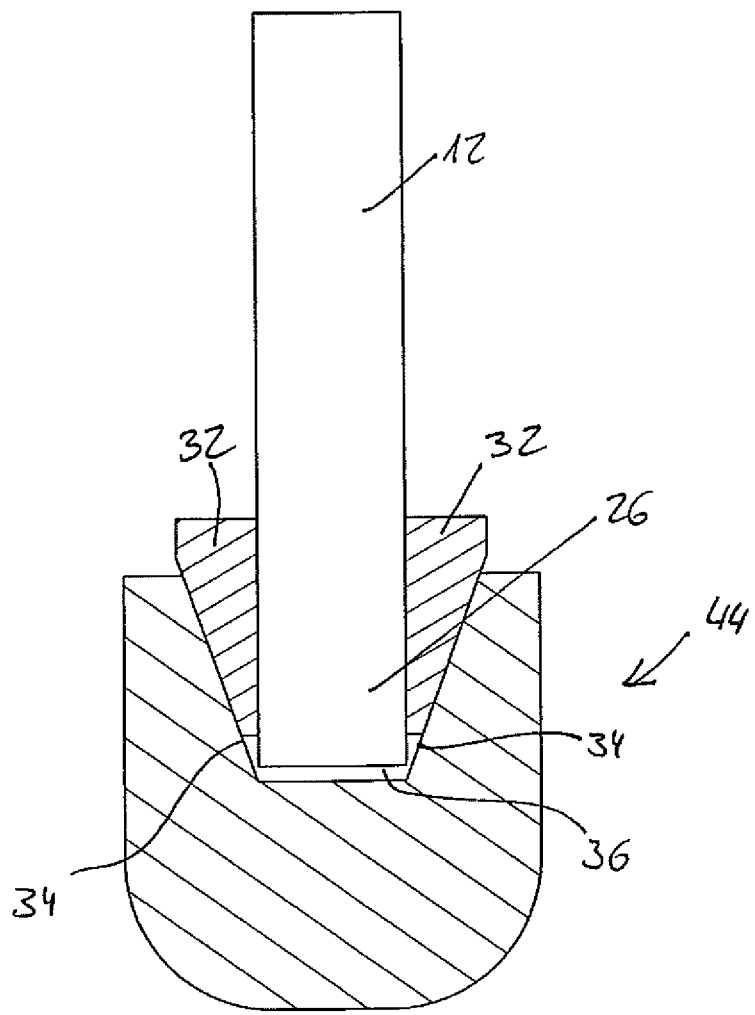
FIG. 15 shows the schematic sectional view through a component with a functional component.

FIG. 15 shows a functional component 44 which is mounted on the end 26 of a component 12. For this purpose, the functional component 44 has the receiving space 36, in which two displacement wedges 32 are arranged in the present case. In the illustrative embodiment shown in FIG. 15, these displacement wedges 32 can be displaced upward and downward and thus ensure that the component 12 is firmly clamped in the receiving space 36, such that it can be secured by a connection element not shown in FIG. 15. The functional component 44 has two displacement surfaces 34 along which the two displacement wedges 32 can be moved. Particularly in the case where only one displacement wedge 32 is present, the latter can be connected to the additional element 15, as is shown in FIG. 14. The clamping action is then obtained when the element 15 is pushed on.

The lower part of FIG. 16 shows a further illustrative embodiment of two components which are connected to each other according to the invention. The lower part of FIG. 16 is a 3D view showing the first component 12 and the second component 2. Two receiving devices 20, through which connection elements 22 can be guided, are shown in the second component 2. Only the sectional views shown in the upper part of FIG. 16 reveal how the two components can be mounted on each other free of play. For this purpose, the first component 12 has receiving elements 14 which, however, are not designed as rail boxes in this illustrative embodiment but instead as frustoconical elevations. It is conceivable here to provide just one of these receiving devices 14, as is shown in the upper right of FIG. 16, or to arrange more than one, for example two conical elevations, on the first component 12, as is shown in the upper left of FIG. 16. On the connection end 4, the second component 2 has depressions 46 which correspond to the truncated cones and into which the frustoconical elevations can engage. The lateral walls of these depressions 46 form in this case the lateral walls 8 which, as can be clearly seen from the sectional views in FIG. 16, taper conically toward each other. The lateral walls of the frustoconical elevations 14 on the first component 12 form the conically tapering stop walls 18. Connection elements 22, for example in the form of a screw, are inserted into the bore extending through both components 2, 12.

An orthopedic technician seeking to connect two components 2, 12 to each other using the embodiment shown in FIG. 16 can do so in a particularly simple way. Thus, for example, merely the first component 12 can be provided from the manufacturer with the frustoconical elevations 14, whereas the second component 2 is supplied without depressions or bores. The two components 2, 12 can be fitted onto each other particularly easily, in particular after cutting the second component 12 to length, such that, through the bores which are contained in the first component 12, corresponding bores can now also be produced in the second component 2 at exactly the correct positions. At the locations thus defined, the frustoconical depressions 46 can also be introduced into the second component 2, such that an exact positioning of the depressions 46 relative to the positions of the frustoconical elevation is possible.

FIG. 17 shows a similar embodiment in which it will be seen, particularly from the 3D view at the bottom, that one of the receiving devices 20 is designed as an oblong hole. From the sectional view shown in the upper left of FIG. 17, it is clear what is achieved by this. While the left-hand elevation 14 bears with its stop walls 18 free of play on the conically tapering lateral walls 8 of the depression 46, this is not the case with the right-hand elevation. Here, a gap 48 forms by which manufacturing tolerances can be compensated. The right-hand elevation serves only as an anti-rotation means, which is intended to prevent a rotation about the longitudinal axis of the left-hand elevation 14. Therefore, the receiving device 20 shown there is designed as an oblong hole, in order to be able to compensate for manufacturing tolerances here and yet be able to insert a connection element 22. In the upper right of FIG. 17, a sectional view is shown that corresponds substantially to the view shown in the upper right of FIG. 16.

FIG. 18 shows a further embodiment corresponding substantially to the embodiment shown in FIG. 16. A 3D view with the first component 12, the second component 2 and two receiving devices 20 is again shown in the lower part. However, in contrast to the views previously shown, the first component 12 is now located on top. From the sectional view shown in the upper part of FIG. 18, it will be seen that the first component 12 and the two illustrated frustoconical elevations, which form the receiving elements 14, are not configured in one piece, but that the receiving elements 14 are let into the first component 12, for example via screw connections. The second component 2 again has corresponding depressions 46 which, with their lateral walls 8, bear in a manner free of play on the conically tapering stop walls 18 of the receiving elements 14.

Figure 19:
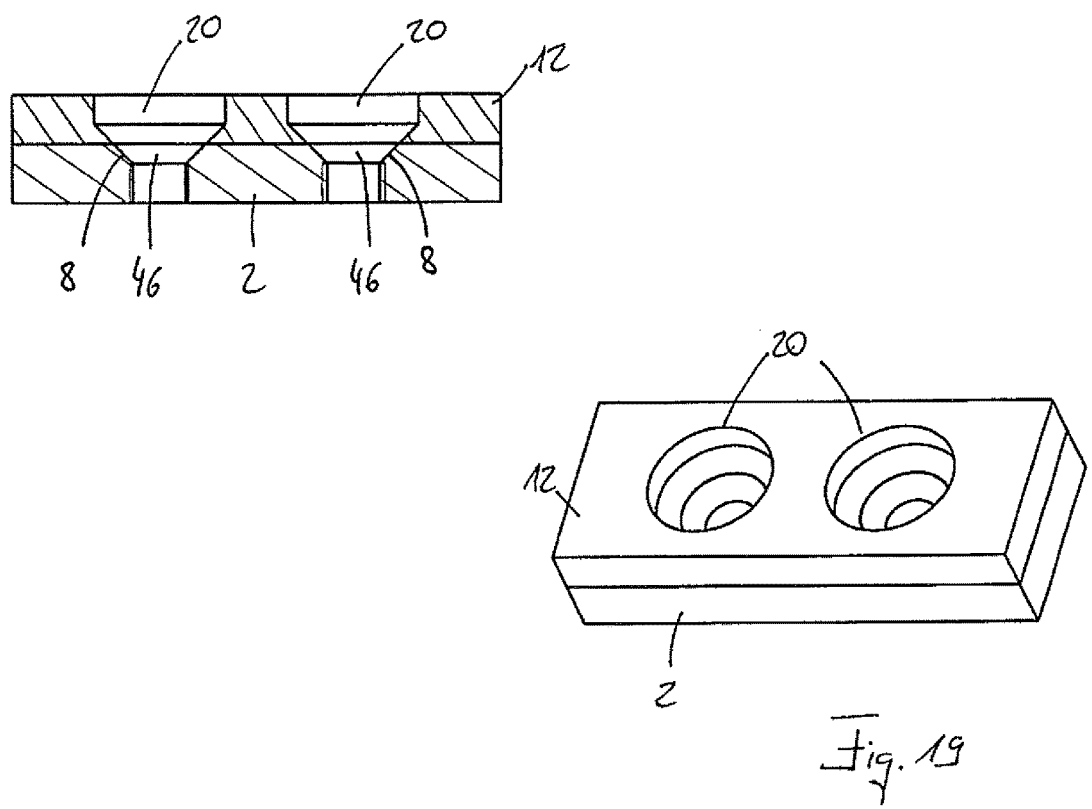

FIG. 19 shows a further embodiment in which the 3D view in the lower part of FIG. 19 differs from the 3D view in FIG. 18 mainly in terms of the size of the receiving devices 20. The sectional view in the upper part of FIG. 19 shows that the second component 2, as is already shown in FIGS. 16 to 18, has depressions 46. These depressions 46 again have conically tapering lateral walls 8. In the sectional view in FIG. 19, the first component 12 is shown only with the receiving devices 20, of which the lateral walls seamlessly continue the lateral walls 8 of the depressions 46. Conical screws can now be inserted into these receiving devices 20, these conical screws having, for example, a frustoconical head whose jacket surface forms the stop walls 18. These also taper conically toward each other, such that this embodiment too is in accordance with the invention.

Figure 20:
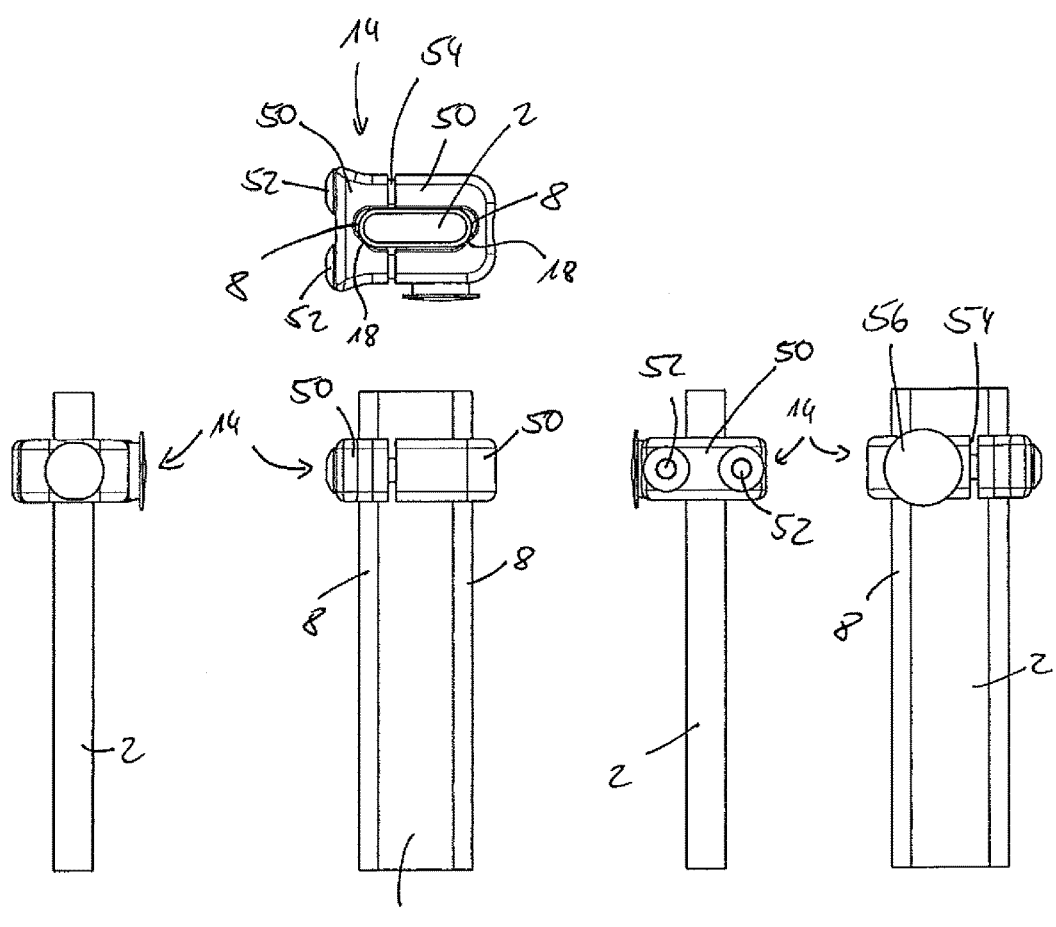
FIGS. 20 and 21 show further views of a possible connection according to a further illustrative embodiment of the present invention.

The second component 2 is shown in four different side views in the lower part of FIG. 20. Above these is a sectional view, which shows a viewing direction along the longitudinal direction of the second component 2. This sectional view in particular shows that the second component 2 has an oval cross section at the connection end 4. The lateral walls 8 thus extend in a curved shape and, starting from the center, i.e. from the broadest point of the second component 2, they therefore taper toward each other seen from the top and underneath in the upper part of FIG. 20. Seen from the center, the width of the second component 2 continuously decreases in this direction, such that the lateral walls 8 taper toward each other.

The receiving element 14, which consists of two clamp elements 50 in the illustrative embodiment shown in FIG. 20, is fitted onto the second component 2. These clamp elements 50 are connected to each other by two screws 52, wherein a space 54 lies between the two clamp elements 50, the width of this space 54 being able to be reduced or increased by screwing in or unscrewing the screws 52. The two clamp elements 50 form a recess which, at least on one side, has stop walls 18 extending obliquely to each other, as can be seen in the upper part of FIG. 20 for example. When the screws 52 are actuated, the two clamp elements 50 are moved toward each other and thus clamp the second component 2 free of play.

Figure 21:
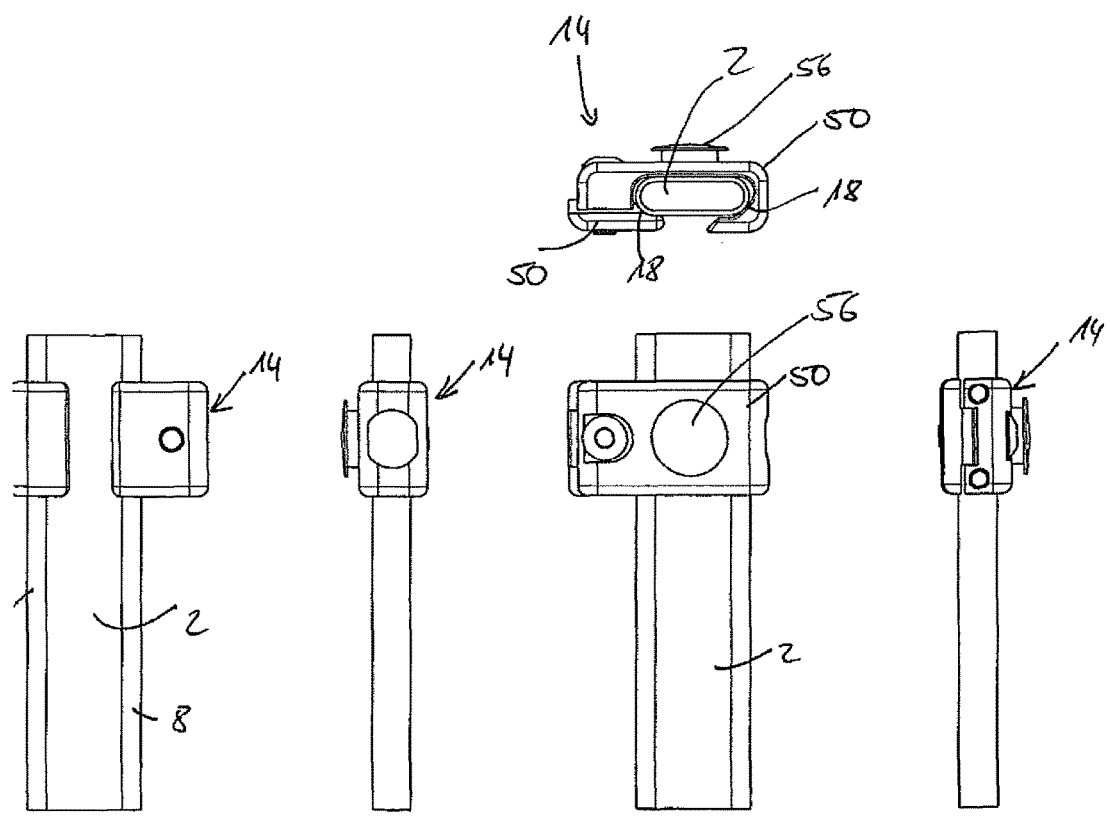

FIG. 21 shows a similar view in which, once again, a receiving element 14 consisting of two clamp elements 50 is fitted onto the second component 2. In the illustrative embodiment shown in FIG. 21, the clamp element 50 shown at the bottom left in the sectional view in the upper part of FIG. 21 is displaceable to the left and to the right. Just like the second clamp element 50, it has in each case an obliquely extending stop wall 18, these tapering conically toward each other. By displacement of the clamp element 50 relative to the second clamp element 50, the two stop walls 18 are moved toward each other or away from each other, such that the second component 2 is clamped and a connection free of play is thus obtained. In FIG. 20 and also in FIG. 21, the receiving element 14 has a securing element 56, which is shown as having a circular shape and on which, for example, straps can be secured that can be placed around the body of a person wearing a rail system of this kind.

LIST OF REFERENCE SIGNS $L_1$ first longitudinal direction
$L_2$ second longitudinal direction
2 second component
4 connection end
6 underside
8 lateral wall
10 bore
12 first component
14 rail box
16 base
18 stop wall
20 receiving device
22 connection element
24 recess
26 end
28 connection end component
30 second connection element
32 displacement wedge
34 displacement surface
36 receiving space
38 rounded corner
40 adapter element
42 nut
44 functional component
46 depression
48 gap
50 clamp element
52 screws
54 space
56 securing element

The invention claimed is:

1. An orthopedic rail system, comprising:
a first component with a receiving element;
a second component with a connection end for connecting to the receiving element;
wherein
the receiving element has two stop walls lying opposite each other;
the connection end has two lateral walls lying opposite each other;
the receiving element and the connection end are connectable to each other by at least one connection element, such that the lateral walls bear on the stop walls in the connected state;
the stop walls and the lateral walls, respectively, taper conically toward each other; and
the receiving element and the connection end are able to be positioned steplessly relative to each other.

2. The rail system as claimed in claim 1, wherein the second component has a second longitudinal direction, and at least one lateral wall encloses, with the second longitudinal direction, an angle different than 0°.

3. The rail system as claimed in claim 2, wherein both stop walls or both lateral walls or both stop walls and also both lateral walls enclose, with the respective first longitudinal direction or second longitudinal direction, an angle different than 0°.

4. The rail system as claimed in claim 3, wherein the angles between the stop walls and the first longitudinal direction and also between the lateral walls and the second longitudinal direction are identical.

5. The rail system as claimed in claim 1, wherein the receiving element has a base and the connection end has an underside, wherein the underside bears on the base in the connected state.

6. The rail system as claimed in claim 1, wherein the rail system has at least one connection element for connecting the receiving element to the connection end.

7. The rail system as claimed in claim 1, wherein the first component has a first longitudinal direction, and at least one stop wall encloses, with the first longitudinal direction, an angle different than 0°.

8. The rail system as claimed in claim 1, wherein the receiving element and the connection end are able to be positioned steplessly relative to each other in two mutually perpendicular directions and are connectable to each other.

9. The rail system as claimed in claim 1, wherein the receiving element is connected releasably to the first component.

10. The rail system as claimed in claim 1, wherein one of the stepless positions of the receiving element relative to the connection end is a position in which the receiving element and the connection end bear on each other in a manner free of play.

\* \* \* \* \*